United States Patent
Gotman et al.

(10) Patent No.: US 6,591,132 B2
(45) Date of Patent: Jul. 8, 2003

(54) ARTIFACT DETECTION IN ENCEPHALOGRAM DATA USING AN EVENT MODEL

(75) Inventors: Jean Gotman, Westmount (CA); YunHua Wang, Toronto (CA); Rajeev Agarwal, Dollard-des-Ormeaux (CA); Danny Flanagan, Montreal West (CA)

(73) Assignee: Stellate Systems Inc., Westmount (CA)

(*) Notice: Subject to any disclaimer, the term of this patent is extended or adjusted under 35 U.S.C. 154(b) by 0 days.

(21) Appl. No.: 09/996,587

(22) Filed: Nov. 30, 2001

(65) Prior Publication Data

US 2003/0105408 A1 Jun. 5, 2003

(51) Int. Cl.[7] .................. A61B 5/04; A61B 110/00
(52) U.S. Cl. .................. 600/544; 128/920; 128/923
(58) Field of Search ................. 600/544, 545, 600/300, 920, 923, 924, 925

(56) References Cited

U.S. PATENT DOCUMENTS

| | | | |
|---|---|---|---|
| 3,841,309 A | * 10/1974 | Salter et al. | 600/544 |
| 4,417,592 A | * 11/1983 | John | 600/544 |
| 4,846,190 A | * 7/1989 | John | 227/151 |
| 5,047,930 A | * 9/1991 | Martens et al. | 600/301 |
| 5,331,876 A | * 7/1994 | Hayden, Sr. | 83/661 |

OTHER PUBLICATIONS

An Efficient Algorithm for Computing Multishell Spherical Volume Conductor Models in EEG Dipole Source Localization; Minguy Sun, IEEE Transactions on Biomedical Engineering, vol. 44, No. 12; Dec. 1997; pp 1243 to 1252.

* cited by examiner

Primary Examiner—Max F. Hindenburg
Assistant Examiner—Navin Natnithithadha

(57) ABSTRACT

A machine-readable storage medium containing a program element for execution by a computing device for performing spike and artifact detection in EG data. The program element comprises a spike detection module for processing EG data to detect spikes. Each spike is a candidate having a likelihood of being related to a physiological event of interest. The program element further comprises an artifact detection module. The artifact detection module is operative to compute respective models of events manifested by the respective spikes detected by the spike detection module, to use the computed models to determine which spikes among the spikes detected by the spike detection module have a high likelihood of being artifacts, to filter the spikes detected by the spike detection module on the basis of the computed models to produce filtered data and to output the filtered data.

33 Claims, 2 Drawing Sheets

ARTIFACT DETECTION IN ENCEPHALOGRAM DATA USING AN EVENT MODEL

FIELD OF THE INVENTION

The invention relates to the art of artifact detection, in particular to an apparatus and a method for detecting artifacts in encephalogram (EG) data.

BACKGROUND OF THE INVENTION

In many cases, only a small portion of encephalogram (EG) data is of interest to a user. Typically, EG data comprises a plurality of data channels acquired using respective electrodes located on a human or animal head. The EG data may comprise features of interest, such as spikes, and large portions of data irrelevant for a particular application.

Furthermore, when the features of interest are spikes, not all the spikes observed in the EG data relate to a physiological event of interest. For example, a spike related to a physiological event of interest may be an epileptiform transient in an electroencephalogram (EEG) and an irrelevant spike, referred to as an artifact, may be either related to an eye movement or an electrode-caused artifact. Sometimes, the identification of spikes related to a physiological event of interest can even be difficult for experienced encephalographers.

Against this background, there exists a need in the industry to provide a novel method and apparatus to detect spikes having a high likelihood of being artifacts.

SUMMARY OF THE INVENTION

In a first broad aspect, the invention provides a machine-readable storage medium containing a program element for execution by a computing device for performing spike and artifact detection in EG data. The program element comprises a spike detection module for processing EG data to detect spikes. Each spike is a candidate having a likelihood of being related to a physiological event of interest. The program element further comprises an artifact detection module. The artifact detection module is operative to compute respective models of events manifested by the respective spikes detected by the spike detection module, to use the computed models to determine which spikes among the spikes detected by the spike detection module have a high likelihood of being artifacts, to filter the spikes detected by the spike detection module on the basis of the computed models to produce filtered data and to output the filtered data.

An advantage provided by the invention is the filtering of the EG data through the identification of highly likely artifacts. Consequently, spikes having a high likelihood of being related to a physiological event of interest can be identified more easily. This may be advantageous in reducing the amount of data to be presented for interpretation by a user. Furthermore, the identification of highly likely artifacts may identify spikes that may be hard to identify as unrelated to a physiological event of interest by the user.

An event is a cause of an observable spike in one or more channels of EG data. The EG data may be electroencephalogram (EEG) data or magnetoencephalogram (MEG) data, among others. An event may be physiological or not. A physiological event is an event produced by the physiology of the human or animal from which the EG data is acquired. Very specific non-limiting examples of physiological events include activation corresponding to an eye movement and brain activity producing an epileptiform transient or sleep transient. A non-limiting example of a non-physiological event is an electrode displacement.

An artifact is any spike that does not relate to a physiological event of interest. For the purpose of this specification, a physiological event of interest relates to one or more events that a user is interested in identifying in the EG data. Examples of physiological events of interest include physiological events producing epileptiform transients or sleep transients, such as vertex sharp waves, among others. An artifact may be related to a non-physiological event. Alternatively an artifact may be related to a physiological event, that event being of no interest to the user.

In a specific and non-limiting example of implementation, the computation of the model of the event manifested by the spike that the artifact detection module computes includes computing a dipole equivalent of the event through the computation of one or more characterizing elements. Specific examples of characterizing elements include the location and the eccentricity of the dipole equivalent as well as the residual variance associated with the dipole equivalent. Preferably, the time instant at which the dipole equivalent is to be computed is determined solely from the EG data, without any user intervention. Alternatively, the user may enter rules related to the determination of the time instant or provide interactive inputs to the program element for guiding the computation of the time instant.

The artifact detection module uses criteria based on one or more characterizing elements of The model, which may be a dipole equivalent, to determine if a spike has a high likelihood of being an artifact. In a first variant, the characterizing element is the location of a dipole equivalent in a two-dimensional or three-dimensional space. If the location of the dipole equivalent is unlikely to be related to a physiological event of interest, then the spike can be characterized as being highly likely an artifact. For example, the location of the dipole equivalent may indicate that the spike is related to eye movement, and therefore has a small likelihood of being an epileptiform transient. In other variants, the artifact detection module relies on the residual variance or eccentricity of the dipole equivalent. In a further variant the artifact detection module relies on a combination of characterizing elements, such as those mentioned herein above. The reader skilled in the art will appreciate that other characterizing elements may be used without departing from the spirit of the invention.

The criteria used by the artifact detection module may be a threshold above which or below which a characterizing element of the model indicates that the spike is highly likely an artifact. Alternatively, the criteria may be an interval of values for which the characterizing element of the model indicates that the spike is highly likely an artifact. The criteria may also be a combination of intervals, thresholds or both for one or more characterizing elements.

As indicated previously, the spikes detected by the spike detection module are filtered on the basis of the computed models. The purpose of the filtering step is to separate for the user who will ultimately analyze the data spikes that are highly likely to be related to physiological events of interest from spikes that are highly likely artifacts. There are many ways in which the filtered information can be presented to the user. The extent to which a spike is highly likely and artifact or highly likely related to a physiological event of interest is determined through the criteria used by the artifact detection module. In a non-limiting example of implementation, the filtering performed by the artifact detection module specifically identifies each spike as highly likely being either an artifact or related to a physiological event of interest. Another possibility is to simply remove the spikes that are highly likely artifacts such that the user only sees the spikes determined to be highly likely physiological events of interest.

In a second broad aspect, the invention provides a machine-readable storage medium containing a program element for execution by a computing device for performing artifact detection in EEG data. Tile program element comprises an input for receiving data derived from an EG and representative of spikes, each spike being a candidate having a likelihood of being related to a physiological event of interest. The program element further comprises an artifact detection module for receiving the data representative of spikes and being operative for computing respective models of events manifested by the respective spikes and using the computed models to determine which spikes among the spikes detected by the spike detection module are highly likely to be artifacts. The program element is further adapted to output data representative of spikes allowing to distinguish in tile data the spikes determined to highly likely be artifacts.

In a third broad aspect, the invention provides a method for performing artifact detection in EEG data.

BRIEF DESCRIPTION OF THE DRAWINGS

A detailed description of examples of implementation of the present invention is provided hereinbelow with reference to the following drawings, in which.

Figure 1:
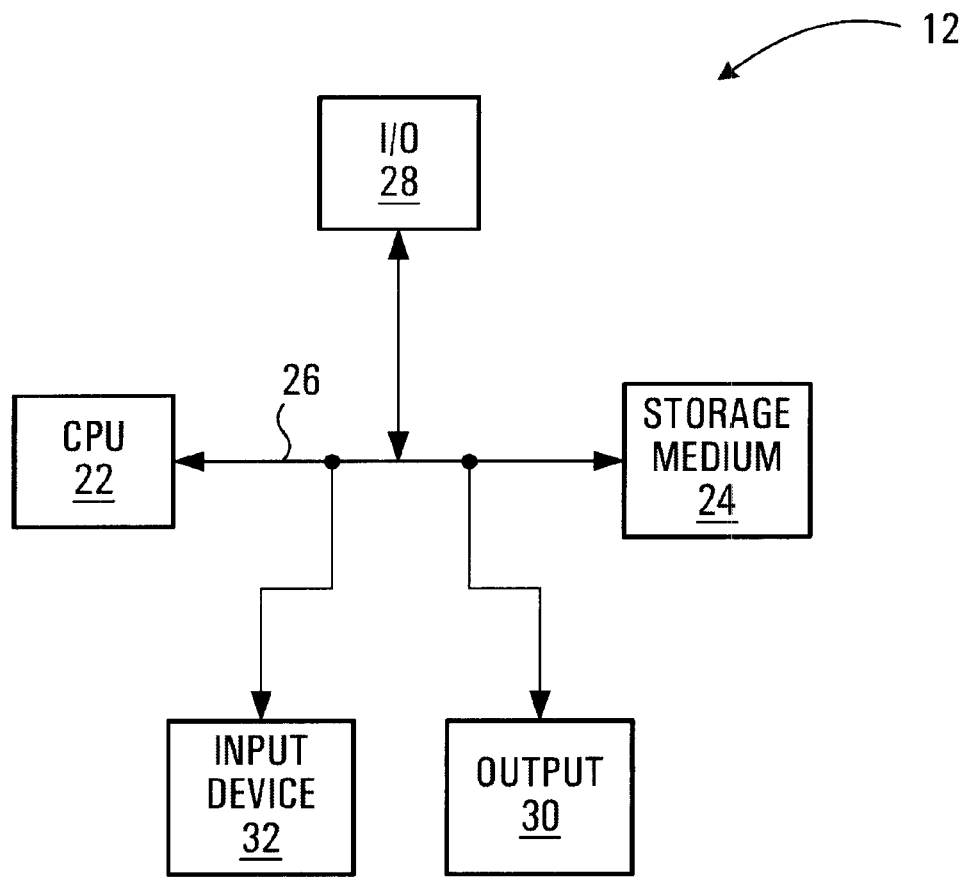
FIG. 1 is a block diagram of a spike detection and artifact detection apparatus.

In the drawings, embodiments of the invention are illustrated by way of example. It is to be expressly understood that the description and drawings are only for purposes of illustration and as an aid to understanding, and are not intended to be a definition of the limits of the invention.

DETAILED DESCRIPTION

FIG. 1 is a block diagram of a spike and artifact detection apparatus in the form of a computing device 12. The computing device 12 includes a Central Processing Unit (CPU) 22 connected to a storage medium 24 over a data bus 26. Although the storage medium 24 is shown as a single block, it may include a plurality of separate components, such as a floppy disk drive, a fixed disk, a tape drive and a Random Access Memory (RAM), among others. The computing device 12 also includes an Input/Output (I/O) interface 28 that connects to the data bus 26. The computing device 12 communicates with outside entities through the I/O interface 28. In a non-limiting example of implementation, the I/O interface 28 is a network interface. In a further non-limiting example of implementation, the I/O interface is a port for exchanging electrical signals with an EG acquisition system.

The computing device 12 also includes an output device 30 to communicate information to a user. In the example shown, the output device 30 includes a display. Optionally, the output device 30 includes a printer or a loudspeaker. The computing device 12 further includes an input device 32 through which the user may input data or control the operation of a program element executed by the CPU 22. The input device 32 may include, for example, any one or a combination of the following: keyboard, pointing device, touch sensitive surface or speech recognition unit.

When the computing device 12 is in use, the storage medium 24 holds a program element executed by the CPU 22, the program element implementing a method for performing spike and artifact detection in EG data.

In a first specific example of implementation, the program element includes an optional spike detection module for processing EG data. The EG data may be EG data stored in the storage medium 24. Alternatively, the EG data may be conveyed to the computing device 12 thorough the I/O interface 28. In this latter case, the EG data may be EG data acquired previously and stored remotely or EG data acquired in real time. The spike detection module detects spikes having a likelihood of being related to a physiological event of interest. Methods for detecting such spikes are known in the art and will therefore not be described in details. For more information, the reader may refer to: Gotman J, Gloor P., Automatic recognition and quantification of interictal epileptic activity in the human scalp EEG, Electroencephalogr Clin Neurophysiol, 1976 November;41(5):513–29, which is herein incorporated by reference. The spike detection module outputs data representative of spikes. In a variant, the spike detection module is not necessary. This is especially the case if the EG data is already treated to produce data representative of spikes.

The program element further comprises an artifact detection module that receives data representative of spikes having a likelihood of being related to a physiological event of interest, either from the spike detection module or directly from the storage medium 24 or from the I/O interface 28. The artifact detection module filters the data representative of spikes to separate for the user who will ultimately analyze the data, spikes that are highly likely to be related to physiological events of interest from spikes that are highly likely artifacts.

Figure 2:
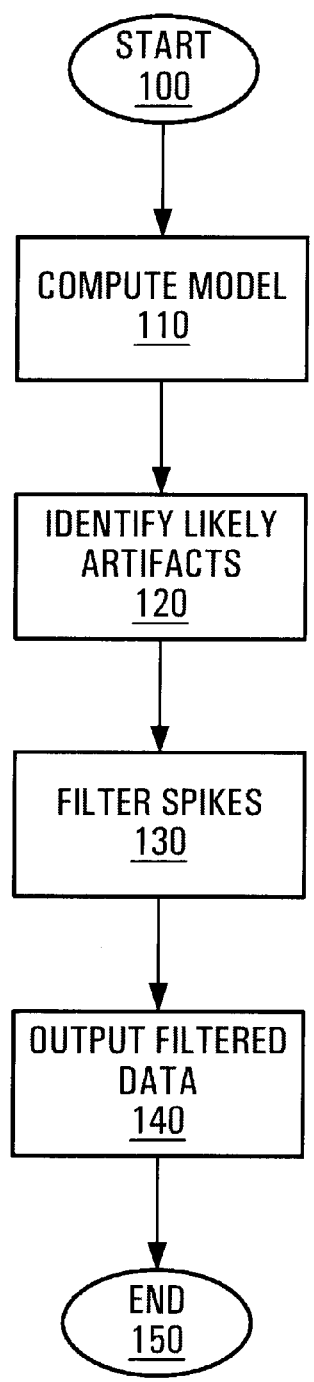
FIG. 2 is a flow chart illustrating the operation of the spike detection module comprised in a program element executed by the spike and artifact detection apparatus.

FIG. 2 is a flowchart of a method implemented by the spike detection module for artifact identification. The method starts at step 100. Then, at step 110, models of events manifested by the spikes detected by the spike detection module or received by an input are computed. At step 120, the computed models are used to determine which spikes are highly likely to be artifacts. The spikes are then filtered at step 130 on the basis of the computed models to produce filtered data, and the filtered data is output at step 140. Finally, the method terminates at step 150.

The models computed at step 110 are used to represent events that may have caused the spikes in the EEG data. In a specific and non-limiting example of implementation, the model used is a dipole model, an example of which is described in Sun M., An efficient algorithm for computing multishell spherical volume conductor models in EEG dipole source localization, IEEE Trans Biomed Eng 1997;44:1243–1252., which is herein incorporated by reference.

Preferably, but not exclusively, the dipole model is computed for each spike at a time instant determined from the EG data, without intervention from the user. In a non-limiting example of implementation, the time instant is determined by the time at which a global field power within a time window around the apex of a spike is maximal. In a variant, the time instant is determined by using user-specified thresholds in addition to the method specified above. Other methods for determining the time instant may be used without departing from the spirit of the invention.

In specific examples of implementation, the dipole equivalents are characterized at least partly by their location in space or at least partly by a waveform representing the time evolution of the events associated with the dipole equivalents. In a further specific example of implementation, the dipole equivalents are characterized by an eccentricity, which is a measure of the distance between an origin in space and the dipole equivalent location, the distance being relative to the radius of a spherical model of a head. Therefore, eccentricity is a non-dimensional number. The dipole equivalents location may be computed either in a two-dimensional or in a three-dimensional space. In another specific example of implementation, the dipole equivalents are characterized by a residual variance, which is indicative of an extent to which the events associated with the dipole equivalents can be modeled by the dipole equivalents. In other words, the residual variance is indicative of whether a dipole equivalent is a good or a poor model for the event. It will be readily apparent to someone skilled in the art that the dipole equivalents may be characterized by a plurality of characteristics, some of which may be those specified herein above.

In a specific example of implementation, the identification of spikes highly likely to be artifacts performed at step 120 compares a characterizing element of the dipole equivalent to at least one threshold. If the numerical value of the characterizing element is either below or above the at least one threshold, depending on the characterizing element, the spike is identified as being highly likely an artifact. The exact value of the at least one threshold is to be specified according to the particular application pursued by the user. Alternatively, the spikes highly likely to be artifacts may be identified through comparison of the characterizing element with interval of values or with a comparison with a plurality of thresholds. Furthermore, the spikes likely to be artifacts may be identified through the comparison of a plurality of characterizing elements with a plurality of thresholds.

In a very specific example of implementation, a residual variance exceeding 0.2 or an eccentricity exceeding 0.9999 is used to detect artifacts highly unlikely to be epileptiform transients.

In a further very specific example of implementation, an artifact is a spike caused by an eye movement. While this type of event is a physiological event, it is not of interest to a user wanting to study events causing epileptiform transients, for example. In this case, by centering the origin of a three-dimensional space on the head of a subject from which the EEG data is acquired, artifacts caused by eye movements may be detected as those having a dipole location below the origin and towards the front of the head by more than half the head radius, an eccentricity greater than 0.95 and a waveform duration of more than 180 ms. The waveform duration is defined as the time elapsed between the peak of the spike detected by the spike detection module and the return to a baseline of the data representative of the spike before the peak, added to the same time interval determined from the data after the peak. Using these thresholds produces a high specificity and a high sensitivity in artifact detection.

The thresholds may be predetermined or specified by the user. In this latter case, they may be provided to the program element through the input device 30 according to predetermined criteria or according to results from test data comprising spikes for which classification as an artifact or not has been performed using a known method. Methods for determining threshold using test data are known in the art and will not be described in further detail.

The filtering of the spikes performed at step 130 is any process performed on the spikes according to whether or not the spike as been identified as a highly likely artifact at step 120. The purpose of the filtering step is to separate for the user who will ultimately analyze the data, spikes that are highly likely to be related to physiological events of interest from spikes that are highly likely artifacts. Specific variants of filtering include removal of spikes that are highly likely artifacts and designation of spikes that are highly likely artifacts in an output data stream, among others. Accordingly, the filtered data output at step 140 may comprise only spikes identified as highly likely related to a physiological event of interest. Examples of such spikes include epileptiform transients and sleep transients, among others. Alternatively, all the spikes may be output along with markers allowing the identification of spikes by the user as highly likely to be either artifacts or spikes related to a physiological event of interest. In non-limiting examples of implementation, the data output may be in the form of a file stored in the storage medium 24, or in the form of graphical data provided at the output 30.

Although various embodiments have been illustrated, this was for the purpose of describing, but not limiting, the invention. Various modifications will become apparent to those skilled in the art and are within the scope of this invention, which is defined more particularly by the attached claims.

What is claimed is:

1. A machine readable storage medium containing a program element for execution by a computing device for performing spike and artifact detection in encephalogram (EG) data, said program element, comprising:
    a) a spike detection module for processing EG data to detect spikes, each spike being a candidate having a likelihood of being related to a physiological event of interest;
    b) an artifact detection module, said artifact detection module being operative for:
        i) spikes detected by said spike detection module, computing respective models of events manifested by the respective spikes;
        ii) use the computed models to determine which spikes among the spikes detected by said spike detection module are highly likely to be artifacts;
        iii) filtering the spikes detected by said spike detection module on the basis of the computed models to produce filtered data; and
        iv) outputting the filtered data.

2. A machine readable storage medium as defined in claim 1 wherein computation of at least one of the respective models includes computing a dipole equivalent to the event.

3. A machine readable storage medium as defined in claim 2 wherein computation of at least one of the respective models includes computing a location of the dipole equivalent.

4. A machine readable storage medium as defined in claim 2 wherein computation of at least one of the respective models includes computing a time instant at which the dipole model is to be computed.

5. A machine readable storage medium as defined in claim 4 wherein computation of at least one of the respective models includes computing a time instant at which the dipole model is to be computed without user's intervention.

6. A machine readable storage medium as defined in claim 3 wherein computation of at least ones of the respective models includes computing the location of the dipole equivalent in a three-dimensional space.

7. A machine readable storage medium as defined in claim 3 wherein computation of at least one of the respective models includes computing the location of the dipole equivalent in a two-dimensional space.

8. A machine readable storage medium as defined in claim 2 wherein computation of at least one of the respective models includes computing an eccentricity of the dipole equivalent.

9. A machine readable storage medium as defined in claim 2 wherein computation of at least ones of the respective model includes computing a residual variance of the dipole equivalent.

10. A machine readable storage medium as defined in claim 1 wherein the physiological event of interest is related to an epileptiform transient.

11. A machine readable storage medium as defined in claim 1 wherein the physiological event of interest is related to a sleep transient.

12. A machine readable storage medium as defined in claim 1 wherein said artifact detection module is operative to determine whether a spike is highly likely to be an artifact at least in part on a basis of a location of a dipole equivalent of the event manifested by the spike.

13. A machine readable storage medium as defined in claim 1 wherein said artifact detection module is operative to determine whether a spike is highly likely to be an artifact at least in part on a basis of an eccentricity of a dipole equivalent of the event manifested by the spike.

14. A machine readable storage medium as defined in claim 1 wherein said artifact detection module is operative to determine whether a spike is highly likely to be an artifact at least in part on a basis of a residual variance of a dipole equivalent of the event manifested by the spike.

15. A machine readable storage medium as defined in claim 1 wherein the EG data is electroencephalogram (EEG) data.

16. A machine readable storage medium as defined in claim 1 wherein the EG data is magnetoencephalogram (MEG) data.

17. A machine readable storage medium containing a program element for execution by a computing device for performing artifact detection in EG data, said program element, comprising:
   a) an input for receiving data derided from an EG and representative of spikes, each spike being a candidate having a likelihood of being related to a physiological event of interest;
   b) an artifact detection module, said artifact detection module receiving the data representative of spikes and being operative for:
      i) computing respective models of events manifested by the respective spikes;
      ii) use the computed models to determine which spikes among the spikes detected by said detection module are highly likely to be artifacts;
      iii) outputting data allowing to distinguish in the data representative of spikes the spikes determined to highly likely be artifacts.

18. A machine readable storage medium as defined in claim 17 wherein computation of at least one of the respective models includes computing a dipole equivalent to the event.

19. A machine readable storage medium as defined in claim 18 wherein computation of at least one of the respective models includes computing a location of the dipole equivalent.

20. A machine readable storage medium as defined in claim 18 wherein computation of at least one of the respective models includes computing a time instant at which the dipole model is to be computed.

21. A machine readable storage medium as defined in claim 20 wherein computation of at least one of the respective models includes computing a time instant at which the dipole model is to be computed without user's intervention.

22. A machine readable storage medium as defined in claim 19 wherein computation of at least one of the respective models includes computing the location of the dipole equivalent in a three-dimensional space.

23. A machine readable storage medium as defined in claim 19 wherein computation of at least one of the respective models includes computing the location of the dipole equivalent in a two-dimensional space.

24. A machine readable storage medium as defined in claim 18 wherein computation of at least one of the respective models includes computing an eccentricity of the dipole equivalent.

25. A machine readable storage medium as defined in claim 18 wherein computation of at least one of the respective model includes computing a residual variance of the dipole equivalent.

26. A machine readable storage medium as defined in claim 17 wherein the physiological event of interest is related to an epileptiform transient.

27. A machine readable storage medium as defined in claim 17 wherein the physiological event of interest is related to a sleep transient.

28. A machine readable storage medium as defined in claim 17 wherein said artifact detection module is operative to determine whether a spike is highly likely to be an artifact at least in part on a basis of a location of a dipole equivalent of the event manifested by the spike.

29. A machine readable storage medium as defined in claim 17 wherein said artifact detection module is operative to determine whether a spike is highly likely to be an artifact at least in part on a basis of an eccentricity of a dipole equivalent of the event manifested by the spike.

30. A machine readable storage medium as defined in claim 17 wherein said artifact detection module is operative to determine whether a spike is highly likely to be an artifact at least in part on a basis of a residual variance of a dipole equivalent of the event manifested by the spike.

31. A machine readable storage medium as defined in claim 17 wherein the EG data is electroencephalogram (EEG) data.

32. A machine readable storage medium as defined in claim 17 wherein the EG data is magnetoencephalogram (MEG) data.

33. A method for performing artifact detection in EG data, comprising:
   a) receiving data derived from an EG and representative of spikes, each spike being a candidate having a likelihood of being related to a physiological event of interest;
      i) computing, from the data derived from an EG, respective models of events manifested by the respective spikes;
      ii) using the computed models to determine which spikes among the spikes detected by said detection module are likely to be artifacts;
      iii) outputting data allowing to distinguish in the data representative of spikes the spikes determined to likely be artifacts.

* * * * *